US008986940B2

(12) United States Patent
McNulty et al.

(10) Patent No.: US 8,986,940 B2
(45) Date of Patent: Mar. 24, 2015

(54) DETECTING INFECTION IN REDUCED PRESSURE WOUND TREATMENT

(71) Applicant: KCI Licensing, Inc., San Antonio, TX (US)

(72) Inventors: Amy K. McNulty, San Antonio, TX (US); Deepak V. Kilpadi, San Antonio, TX (US); George Hutchinson, San Antonio, TX (US); Nancy Price, San Antonio, TX (US)

(73) Assignee: KCI Licensing, Inc., San Antonio, TX (US)

( * ) Notice: Subject to any disclaimer, the term of this patent is extended or adjusted under 35 U.S.C. 154(b) by 0 days.

(21) Appl. No.: 13/890,096

(22) Filed: May 8, 2013

(65) Prior Publication Data

US 2013/0244899 A1 Sep. 19, 2013

Related U.S. Application Data

(62) Division of application No. 12/477,704, filed on Jun. 3, 2009, now Pat. No. 8,460,892.

(60) Provisional application No. 61/058,819, filed on Jun. 4, 2008, provisional application No. 61/118,161, filed on Nov. 26, 2008.

(51) Int. Cl.
| | | |
|---|---|---|
| *C12Q 1/66* | (2006.01) | |
| *A61B 5/00* | (2006.01) | |
| *A61B 5/145* | (2006.01) | |
| *A61B 5/1459* | (2006.01) | |
| *A61L 15/38* | (2006.01) | |
| *A61L 15/42* | (2006.01) | |
| *A61M 1/00* | (2006.01) | |
| *G01N 33/569* | (2006.01) | |
| *G01N 33/68* | (2006.01) | |
| *A61B 19/08* | (2006.01) | |
| *C12Q 1/04* | (2006.01) | |
| *C12Q 1/37* | (2006.01) | |
| *C12Q 1/68* | (2006.01) | |

(52) U.S. Cl.
CPC .............. *A61B 5/0082* (2013.01); *A61B 5/145* (2013.01); *A61B 5/14546* (2013.01); *A61B 5/1459* (2013.01); *A61B 5/445* (2013.01); *A61L 15/38* (2013.01); *A61L 15/425* (2013.01); *A61M 1/0088* (2013.01); *C12Q 1/66* (2013.01); *G01N 33/56911* (2013.01); *G01N 33/6893* (2013.01); *A61B 19/08* (2013.01); *C12Q 1/04* (2013.01); *C12Q 1/37* (2013.01); *C12Q 1/689* (2013.01); *A61M 1/0025* (2013.01); *A61M 2202/20* (2013.01); *A61M 2205/3306* (2013.01); *A61M 2205/583* (2013.01); *G01N 2800/26* (2013.01)
USPC ................................ 435/8; 435/4; 435/287.1

(58) Field of Classification Search
None
See application file for complete search history.

(56) References Cited

U.S. PATENT DOCUMENTS

| | | | |
|---|---|---|---|
| 1,355,846 | A | 10/1920 | Rannells |
| 2,547,758 | A | 4/1951 | Keeling |
| 2,632,443 | A | 3/1953 | Lesher |
| 2,682,873 | A | 7/1954 | Evans et al. |
| 2,910,763 | A | 11/1959 | Lauterbach |
| 2,969,057 | A | 1/1961 | Simmons |
| 3,066,672 | A | 12/1962 | Crosby, Jr. et al. |
| 3,367,332 | A | 2/1968 | Groves |
| 3,520,300 | A | 7/1970 | Flower, Guiles, Jr. |
| 3,568,675 | A | 3/1971 | Harvey |
| 3,648,692 | A | 3/1972 | Wheeler |
| 3,682,180 | A | 8/1972 | McFarlane |
| 3,826,254 | A | 7/1974 | Mellor |
| 4,080,970 | A | 3/1978 | Miller |
| 4,096,853 | A | 6/1978 | Weigand |
| 4,139,004 | A | 2/1979 | Gonzalez, Jr. |
| 4,165,748 | A | 8/1979 | Johnson |
| 4,184,510 | A | 1/1980 | Murry et al. |
| 4,233,969 | A | 11/1980 | Lock et al. |
| 4,245,630 | A | 1/1981 | Lloyd et al. |
| 4,256,109 | A | 3/1981 | Nichols |
| 4,261,363 | A | 4/1981 | Russo |
| 4,275,721 | A | 6/1981 | Olson |
| 4,284,079 | A | 8/1981 | Adair |
| 4,297,995 | A | 11/1981 | Golub |
| 4,333,468 | A | 6/1982 | Geist |
| 4,373,519 | A | 2/1983 | Errede et al. |
| 4,382,441 | A | 5/1983 | Svedman |
| 4,392,853 | A | 7/1983 | Muto |
| 4,392,858 | A | 7/1983 | George et al. |

(Continued)

FOREIGN PATENT DOCUMENTS

| | | |
|---|---|---|
| AU | 550575 A1 | 3/1986 |
| AU | 745271 | 4/1999 |

(Continued)

OTHER PUBLICATIONS

N.A. Bagautdinov, "Variant of External Vacuum Aspiration in the Treatment of Purulent Diseases of the Soft Tissues," Current Problems in Modern Clinical Surgery: Interdepartmental Collection, edited by V. Ye Volkov et al. (Chuvashia State University, Cheboksary, U.S.S.R. 1986);pp. 94-96 (copy and certified translation).

Louis C. Argenta, MD and Michael J. Morykwas, PhD; "Vacuum-Assisted Closure: A New Method for Wound Control and Treatment: Animal Studies & Basic Foundation"; Annals of Plastic Surgery, vol. 38, No. 6, Jun. 1997; pp. 553-562.

Susan Mendez-Eastmen, RN; "When Wounds Won't Heal" RN Jan. 1998, vol. 61 (1); Medical Economics Company, Inc., Montvale, NJ, USA; pp. 20-24.

(Continued)

Primary Examiner — Brian J Gangle

(57) ABSTRACT

Provided is a method of detecting infection in a wound caused by an infecting organism at a wound site. Also provided is a system for detecting an infection in a wound at a wound site. Additionally, a porous pad comprising luciferase is provided.

11 Claims, 3 Drawing Sheets

(56) References Cited

U.S. PATENT DOCUMENTS

| | | |
|---|---|---|
| 4,419,097 A | 12/1983 | Rowland |
| 4,465,485 A | 8/1984 | Kashmer et al. |
| 4,475,909 A | 10/1984 | Eisenberg |
| 4,480,638 A | 11/1984 | Schmid |
| 4,525,166 A | 6/1985 | Leclerc |
| 4,525,374 A | 6/1985 | Vaillancourt |
| 4,540,412 A | 9/1985 | Van Overloop |
| 4,543,100 A | 9/1985 | Brodsky |
| 4,548,202 A | 10/1985 | Duncan |
| 4,551,139 A | 11/1985 | Plaas et al. |
| 4,569,348 A | 2/1986 | Hasslinger |
| 4,605,399 A | 8/1986 | Weston et al. |
| 4,608,041 A | 8/1986 | Nielsen |
| 4,640,688 A | 2/1987 | Hauser |
| 4,655,754 A | 4/1987 | Richmond et al. |
| 4,664,662 A | 5/1987 | Webster |
| 4,710,165 A | 12/1987 | McNeil et al. |
| 4,733,659 A | 3/1988 | Edenbaum et al. |
| 4,743,232 A | 5/1988 | Kruger |
| 4,758,220 A | 7/1988 | Sundblom et al. |
| 4,787,888 A | 11/1988 | Fox |
| 4,826,494 A | 5/1989 | Richmond et al. |
| 4,838,883 A | 6/1989 | Matsuura |
| 4,840,187 A | 6/1989 | Brazier |
| 4,863,449 A | 9/1989 | Therriault et al. |
| 4,872,450 A | 10/1989 | Austad |
| 4,878,901 A | 11/1989 | Sachse |
| 4,897,081 A | 1/1990 | Poirier et al. |
| 4,906,233 A | 3/1990 | Moriuchi et al. |
| 4,906,240 A | 3/1990 | Reed et al. |
| 4,919,654 A | 4/1990 | Kalt et al. |
| 4,941,882 A | 7/1990 | Ward et al. |
| 4,953,565 A | 9/1990 | Tachibana et al. |
| 4,969,880 A | 11/1990 | Zamierowski |
| 4,985,019 A | 1/1991 | Michelson |
| 5,037,397 A | 8/1991 | Kalt et al. |
| 5,086,170 A | 2/1992 | Luheshi et al. |
| 5,092,858 A | 3/1992 | Benson et al. |
| 5,100,396 A | 3/1992 | Zamierowski |
| 5,134,994 A | 8/1992 | Say |
| 5,149,331 A | 9/1992 | Ferdman et al. |
| 5,167,613 A | 12/1992 | Karami et al. |
| 5,176,663 A | 1/1993 | Svedman et al. |
| 5,215,522 A | 6/1993 | Page et al. |
| 5,232,453 A | 8/1993 | Plass et al. |
| 5,261,893 A | 11/1993 | Zamierowski |
| 5,278,100 A | 1/1994 | Doan et al. |
| 5,279,550 A | 1/1994 | Habib et al. |
| 5,298,015 A | 3/1994 | Komatsuzaki et al. |
| 5,342,376 A | 8/1994 | Ruff |
| 5,344,415 A | 9/1994 | DeBusk et al. |
| 5,358,494 A | 10/1994 | Svedman |
| 5,437,622 A | 8/1995 | Carion |
| 5,437,651 A | 8/1995 | Todd et al. |
| 5,527,293 A | 6/1996 | Zamierowski |
| 5,549,584 A | 8/1996 | Gross |
| 5,556,375 A | 9/1996 | Ewall |
| 5,607,388 A | 3/1997 | Ewall |
| 5,636,643 A | 6/1997 | Argenta et al. |
| 5,645,081 A | 7/1997 | Argenta et al. |
| 6,071,267 A | 6/2000 | Zamierowski |
| 6,135,116 A | 10/2000 | Vogel et al. |
| 6,241,747 B1 | 6/2001 | Ruff |
| 6,287,316 B1 | 9/2001 | Agarwal et al. |
| 6,345,623 B1 | 2/2002 | Heaton et al. |
| 6,488,643 B1 | 12/2002 | Tumey et al. |
| 6,493,568 B1 | 12/2002 | Bell et al. |
| 6,553,998 B2 | 4/2003 | Heaton et al. |
| 6,814,079 B2 | 11/2004 | Heaton et al. |
| 2002/0077661 A1 | 6/2002 | Saadat |
| 2002/0115951 A1 | 8/2002 | Norstrem et al. |
| 2002/0120185 A1 | 8/2002 | Johnson |
| 2002/0143286 A1 | 10/2002 | Tumey |
| 2003/0040687 A1 | 2/2003 | Boynton et al. |
| 2003/0050594 A1 | 3/2003 | Zamierowski |
| 2006/0079852 A1 | 4/2006 | Bubb et al. |
| 2008/0077091 A1 | 3/2008 | Mulligan |

FOREIGN PATENT DOCUMENTS

| | | |
|---|---|---|
| AU | 755496 | 2/2002 |
| CA | 2005436 | 6/1990 |
| DE | 26 40 413 A1 | 3/1978 |
| DE | 43 06 478 A1 | 9/1994 |
| DE | 295 04 378 U1 | 10/1995 |
| EP | 0100148 A1 | 2/1984 |
| EP | 0117632 A2 | 9/1984 |
| EP | 0161865 A2 | 11/1985 |
| EP | 0358302 A2 | 3/1990 |
| EP | 1018967 B1 | 8/2004 |
| GB | 692578 | 6/1953 |
| GB | 2 195 255 A | 4/1988 |
| GB | 2 198 789 A | 6/1988 |
| GB | 2 220 357 A | 1/1990 |
| GB | 2 235 877 A | 3/1991 |
| GB | 2 329 127 B | 3/1999 |
| GB | 2 333 965 A | 8/1999 |
| GB | 2340235 A | 2/2000 |
| GB | 2442132 A | 3/2008 |
| JP | 4129536 | 4/1992 |
| SG | 71559 | 4/2002 |
| WO | 80/02182 | 10/1980 |
| WO | 87/04626 | 8/1987 |
| WO | 90/10424 | 9/1990 |
| WO | 93/09727 | 5/1993 |
| WO | 94/20041 | 9/1994 |
| WO | 96/05873 | 2/1996 |
| WO | 97/18007 | 5/1997 |
| WO | 99/13793 | 3/1999 |

OTHER PUBLICATIONS

James H. Blackburn, II, Md, et al; "Negative-Pressure Dressings as a Bolster for Skin Grafts"; Annals of Plastic Surgery, vol. 40, No. 5, May 1998, pp. 453-457.

John Masters; "Reliable, Inexpensive and Simple Suction Dressings"; Letters to the Editor, British Journal of Plastic Surgery, 1998, vol. 51 (3), p. 267; Elsevier Science/The British Association of Plastic Surgeons, UK.

S.E. Greer, et al "The Use of Subatmospheric Pressure Dressing Therapy to Close Lymphocutaneous Fistulas of the Groin" British Journal of Plastic Surgery (2000), vol. 53, pp. 484-487.

George V. Letsou, MD., et al; "Stimulation of Adenylate Cyclase Activity in Cultured Endothelial Cells Subjected to Cyclic Stretch"; Journal of Cardiovascular Surgery, vol. 31, 1990, pp. 634-639.

Orringer, Jay, et al; "Management of Wounds in Patients with Complex Enterocutaneous Fistulas"; Surgery, Gynecology & Obstetrics, Jul. 1987, vol. 165, pp. 79-80.

International Search Report for PCT International Application PCT/GB95/01983; Nov. 23, 1995.

PCT International Search Report for PCT International Application PCT/GB98/02713; Jan. 8, 1999.

PCT Written Opinion; PCT International Application PCT/GB98/02713; Jun. 8, 1999.

PCT International Examination and Search Report, PCT International Application PCT/GB96/02802; Jan. 15, 1998 & Apr. 29, 1997.

PCT Written Opinion, PCT International Application PCT/GB96/02802; Sep. 3, 1997.

Dattilo, Philip P., Jr., et al; "Medical Textiles: Application of an Absorbable Barbed Bi-directional Surgical Suture"; Journal of Textile and Apparel, Technology and Management, vol. 2, Issue 2, Spring 2002, pp. 1-5.

Kostyuchenok, B.M., et al; "Vacuum Treatment in the Surgical Management of Purulent Wounds"; Vestnik Khirurgi, Sep. 1986, pp. 18-21 and 6 page English translation thereof.

Davydov, Yu. A., et al; "Vacuum Therapy in the Treatment of Purulent Lactation Mastitis"; Vestnik Khirurgi, May 14, 1986, pp. 66-70, and 9 page English translation thereof.

(56) References Cited

OTHER PUBLICATIONS

Yusupov. Yu. N., et al; "Active Wound Drainage", Vestnik Khirurgi, vol. 138, Issue 4, 1987, and 7 page English translation thereof.

Davydov, Yu. A., et al; "Bacteriological and Cytological Assessment of Vacuum Therapy for Purulent Wounds"; Vestnik Khirurgi, Oct. 1988, pp. 48-52, and 8 page English translation thereof.

Davydov, Yu. A., et al; "Concepts for the Clinical-Biological Management of the Wound Process in the Treatment of Purulent Wounds by Means of Vacuum Therapy"; Vestnik Khirurgi, Jul. 7, 1980, pp. 132-136, and 8 page English translation thereof.

Chariker, Mark E., M.D., et al; "Effective Management of incisional and cutaneous fistulae with closed suction wound drainage"; Contemporary Surgery, vol. 34, Jun. 1989, pp. 59-63.

Egnell Minor, Instruction Book, First Edition, 300 7502, Feb. 1975, pp. 24.

Egnell Minor: Addition to the Users Manual Concerning Overflow Protection—Concerns all Egnell Pumps, Feb. 3, 1983, p. 1.

Svedman, P.: "Irrigation Treatment of Leg Ulcers", The Lancet, Sep. 3, 1983, pp. 532-534.

Chinn, Steven D. et al.: "Closed Wound Suction Drainage", The Journal of Foot Surgery, vol. 24, No. 1, 1985, pp. 76-81.

Arnljots, Björn et al.: "Irrigation Treatment in Split-Thickness Skin Grafting of Intractable Leg Ulcers", Scand J. Plast Reconstr. Surg., vol. 19, 1985, pp. 211-213.

Svedman, P.: "A Dressing Allowing Continuous Treatment of a Biosurface", IRCS Medical Science: Biomedical Technology, Clinical Medicine, Surgery and Transplantation, vol. 7, 1979, p. 221.

Svedman, P. et al.: "A Dressing System Providing Fluid Supply and Suction Drainage Used for Continuous or Intermittent Irrigation", Annals of Plastic Surgery, vol. 17, No. 2, Aug. 1986, pp. 125-133.

K.F. Jeter, T.E. Tintle, and M. Chariker, "Managing Draining Wounds and Fistulae: New and Established Methods," Chronic Wound Care, edited by D. Krasner (Health Management Publications, Inc., King of Prussia, PA 1990), pp. 240-246.

G. Živadinovic, V. Dukić, Ž. Maksimovio, D. Radak, and P. Peška, "Vacuum Therapy in the Treatment of Peripheral Blood Vessels," Timok Medical Journal 11 (1986), pp. 161-164 (copy and certified translation).

F.E. Johnson, "An Improved Technique for Skin Graft Placement Using a Suction Drain," Surgery, Gynecology, and Obstetrics 159 (1984), pp. 584-585.

A.A. Safronov, Dissertation Abstract, Vacuum Therapy of Trophic Ulcers of the Lower Leg with Simultaneous Autoplasty of the Skin (Central Scientific Research Institute of Traumatology and Orthopedics, Moscow, U.S.S.R. 1967) (copy and certified translation).

M. Schein, R. Saadia, J.R. Jamieson, and G.A.G. Decker, "The 'Sandwich Technique' in the Management of the Open Abdomen," British Journal of Surgery 73 (1986), pp. 369-370.

D.E. Tribble, "An Improved Sump Drain-Irrigation Device of Simple Construction," Archives of Surgery 105 (1972) pp. 511-513.

C.E. Tennant, "The Use of Hypermia in the Postoperative Treatment of Lesions of the Extremities and Thorax," Journal of the American Medical Association 64 (1915), pp. 1548-1549.

Selections from W. Meyer and V. Schmieden, Bier's Hyperemic Treatment in Surgery, Medicine, and the Specialties: A Manual of its Practical Application, (W.B. Saunders Co., Philadelphia, PA 1909), pp. 17-25, 44-64, 90-96, 167-170, and 210-211.

V.A. Solovev et al., Guidelines, The Method of Treatment of Immature External Fistulas in the Upper Gastrointestinal Tract, editor-in-chief Prov. V.I. Parahonyak (S.M. Kirov Gorky State Medical Institute, Gorky, U.S.S.R. 1987) ("Solovev Guidelines").

V.A. Kuznetsov & N.A. Bagautdinov, "Vacuum and Vacuum-Sorption Treatment of Open Septic Wounds," in II All-Union Conference on Wounds and Wound Infections: Presentation Abstracts, edited by B.M. Kostyuchenok et al. (Moscow, U.S.S.R. Oct. 28-29, 1986) pp. 91-92 ("Bagautdinov II").

V.A. Solovev, Dissertation Abstract, Treatment and Prevention of Suture Failures after Gastric Resection (S.M. Kirov Gorky State Medical Institute, Gorky, U.S.S.R. 1988) ("Solovev Abstract").

V.A.C. ® Therapy Clinical Guidelines: A Reference Source for Clinicians (Jul. 2007).

DETECTING INFECTION IN REDUCED PRESSURE WOUND TREATMENT

CROSS-REFERENCE TO RELATED APPLICATIONS

This application is a Divisional of U.S. patent application Ser. No. 12/477,704, entitled "Detecting Infection In Reduced Pressure Wound Treatment", filed Jun. 3, 2009, which claims the benefit of U.S. Provisional Application No. 61/058,819, filed Jun. 4, 2008, and U.S. Provisional Application No. 61/118,161, filed Nov. 26, 2008, both of which are incorporated herein by reference.

BACKGROUND

1. Field of the Invention

The present invention relates generally to tissue treatment systems, and in particular, but not by way of limitation, to methods and compositions for detecting infection in a wound.

2. Description of Related Art

Clinical studies and practice have shown that a system for providing a reduced pressure in proximity to a tissue site augments and accelerates the growth of new tissue at the tissue site. The applications of this phenomenon are numerous, but application of reduced pressure has been particularly successful in treating wounds. This treatment (frequently referred to in the medical community as "negative pressure wound therapy," "reduced pressure therapy," or "vacuum therapy") provides a number of benefits, including faster healing and increased formulation of granulation tissue. Typically, reduced pressure is applied to tissue through a porous pad or other manifolding device. The porous pad contains cells or pores that are capable of distributing reduced pressure to the tissue and channeling fluids that are drawn from the tissue. The porous pad often is incorporated into a dressing having other components that facilitate treatment.

One difficulty associated with the use of such systems is detecting the presence or type of infection present in the wound without disturbing the airtight dressing covering the wound. Numerous methods have been developed relating to the detection of microorganisms. Various forms of those methods include the use of spectrometers, chromatographs, and other electronic sensors for detecting the presence of microorganisms. Exemplary U.S. patents include Lewis, et al., U.S. Pat. No. 6,017,440, issued Jan. 25, 2000; Chutjian, et al., U.S. Pat. No. 6,188,067, issued Feb. 13, 2001; Hunter, et al., U.S. Pat. No. 5,811,255, issued Sep. 22, 1998; Overton, et al., U.S. Pat. No. 5,611,846, issued Mar. 18, 1997; and Yu, U.S. Pat. No. 5,583,281, issued Dec. 10, 1996.

While such systems have been highly successful in the promotion of wound closure, healing many wounds previously thought untreatable, some difficulty remains. Because the very nature of such systems require an atmospherically sealed wound site, it is difficult to detect the presence or concentration of contaminant microorganisms such as bacteria that may be present in the wound site, without removing the wound dressing. It has heretofore been necessary to disturb the wound site, and thereby interrupt the therapy, in order to test for the presence or concentration of bacterial infection. Furthermore, any disturbance to the wound site may increase the possibility of infection to the wound site. Additionally, removal of the wound dressing may cause pain or discomfort to the patient.

Some progress has been made to circumvent these problems with the invention described in United States Patent Application Publication US2002/0143286, incorporated herein by reference. That application describes the use of sensing devices that optically sense the presence of a bacterial agent or other form of infection in the wound fluid. Other methods to more specifically identify and quantify the infectious agent are desirable.

Accordingly, a primary object of the present invention is to provide a vacuum assisted wound closure device that utilizes a means for detecting the presence of an infection present at a wound site during utilization of an airtight dressing without disturbing the dressing at the wound site.

A further object of the present invention is to provide a means for identifying the nature or specific type of infection present at a wound site during the utilization of an airtight dressing without disturbing the dressing at the wound site.

It is yet a further object of the present invention to provide a means for detecting the concentration of an infecting agent present at a wound site during utilization of an airtight dressing without disturbing the dressing at the wound site.

SUMMARY

The problems presented by existing means for detection of infection in reduced pressure treatment are solved by the methods and apparatuses of the illustrative embodiments described herein. In one embodiment, a method of detecting infection in a wound caused by an infecting organism at a wound site is provided that includes applying a reduced pressure to the wound site, withdrawing fluid from the wound site in response to the reduced pressure, collecting the fluid withdrawn from the wound site, and assaying the fluid collected from the wound site for a product of the infection or a component of the infecting organism, whereby the presence of the product or the component indicates the presence of an infection in the wound.

In an additional embodiment, a system for detecting an infection in a wound at a wound site is provided that includes a source of reduced pressure, a porous pad adapted to deliver the reduced pressure to the wound site, a drape adapted to provide a substantially airtight cover over the pad and the wound site, a conduit fluidly connecting the porous pad to the source of reduced pressure whereby fluid is withdrawn from the wound site in response to the reduced pressure, and a device for analyzing the fluid withdrawn from the wound site to identify a product of the infection or a component of an infecting organism, whereby the presence of the product of the component indicates the presence of an infection in the wound.

In a further embodiment, a porous pad adapted for distributing reduced pressure to a wound site us provided that includes luciferase.

Other objects, features, and advantages of the illustrative embodiments will become apparent with reference to the drawings and detailed description that follow.

DETAILED DESCRIPTION

In the following detailed description of the illustrative embodiments, reference is made to the accompanying drawings that form a part hereof. These embodiments are described in sufficient detail to enable those skilled in the art to practice the invention, and it is understood that other embodiments may be utilized and that logical structural, mechanical, electrical, and chemical changes may be made without departing from the spirit or scope of the invention. To avoid detail not necessary to enable those skilled in the art to practice the embodiments described herein, the description may omit certain information known to those skilled in the art. The following detailed description is, therefore, not to be taken in a limiting sense, and the scope of the illustrative embodiments are defined only by the appended claims.

Figure 1:
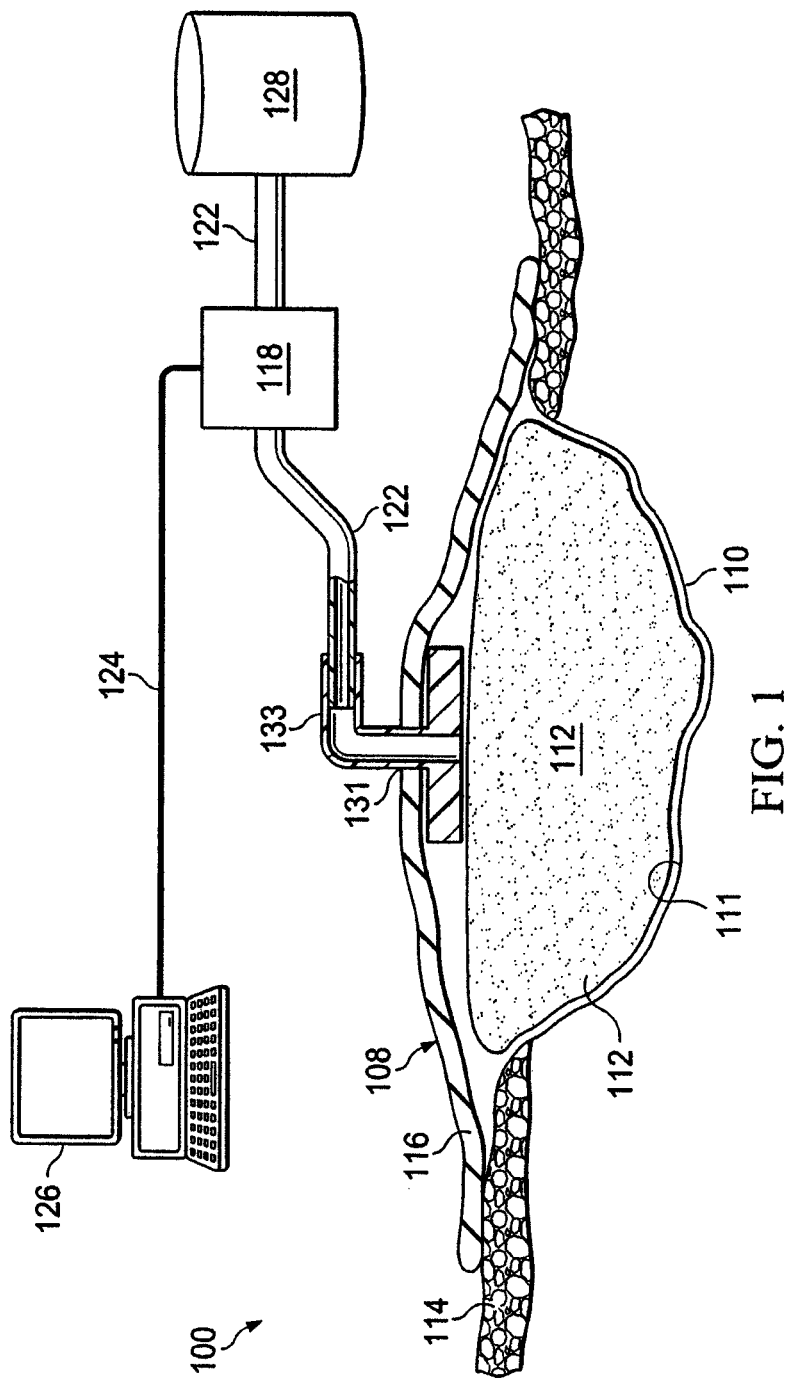
FIG. 1 is a diagram, shown in partial cross-section, of an illustrative embodiment of a reduced-pressure treatment system for detecting infection.

Referring to FIG. 1, an illustrative embodiment of a reduced-pressure treatment system 100 provides reduced-pressure treatment to a tissue site 110, which may include a wound 111, and detects infections in the tissue site 110. The reduced-pressure treatment system 100 includes a reduced-pressure source 128, fluidly connected to a conduit 122, that delivers reduced pressure to the tissue site 110 via a dressing 108. The dressing 108 includes a pad 112 that is disposed in the wound 111. A drape 116 is adhered to the patient's epidermis 114 and provides a fluid seal around the wound 111, allowing the maintenance of reduced pressure on the wound 111. Reduced pressure causes fluid, such as exudate, from the wound 111 to be drawn to a device 118 for analyzing the withdrawn fluid or extract thereof for a product of an infection or a component of an infecting organism or group of organisms.

The wound 111 may be an injury or defect located on or within any tissue site 110, including but not limited to, bone tissue, adipose tissue, muscle tissue, subcutaneous tissue, neural tissue, dermal tissue, vascular tissue, connective tissue, cartilage, tendons or ligaments. The wound 111 may also be any tissue that is not necessarily injured or defected, but instead is an area in which it is desired to add or promote growth of additional tissue.

As used herein, an "infecting organism" is a microorganism (bacteria, fungi, protists, archaea, virus) that can cause wound infection. Non-limiting examples include *Staphylococcus aureus*, *Streptococcus pyrogenes*, *Escherichia coli*, *Pseudomonas aeruginosa*, *Proteus mirabilis*, *Klebsiella pneumoniae*, *Candida albicans* and *Bacteroides fragilis*. This includes (a) specific biotypes of a particular species or genus that has a particular characteristic or makes a particular product, where the characteristic or product can be detected by testing, e.g., *S. aureus* producing toxic shock syndrome toxin-1 (TSST-1); coagulase-negative staphylococci, or Group D streptococci; and (b) a group that has more than one species, e.g., Gram negative bacteria, *Corynebacterium* spp., Enterococci, *Enterobacter* spp., *Streptococcus* spp. In some embodiments, the infecting organism or group of organisms is a bacterium.

As used herein, a "product of an infection" is a specifically identifiable compound produced by either the host (i.e., patient) or the infecting organism during an infection. The host product might also be made when not infected, but for such a product to be useful in the present methods, it should be produced in higher quantities in the fluid drawn from the wound during infection than fluid drawn from an uninfected wound. Nonlimiting examples of products of an infection include adenosine-5'-triphosphate (ATP) (made by bacteria) and certain cytokines, fibronectin fragments, neutrophil proteases, and macrophage protease (made by the host). A specifically identifiable compound is a compound that can be identified individually by its chemical composition or reactivity to a particular reagent such as an antibody or a nucleic acid probe of a particular sequence.

The drape 116 of the dressing 108 may be any material that provides a fluid seal. The drape 116 may, for example, be an impermeable or semi-permeable, elastomeric material. "Elastomeric" means having the properties of an elastomer. It generally refers to a polymeric material that has rubber-like properties. More specifically, most elastomers have elongation rates greater than 100% and a significant amount of resilience. The resilience of a material refers to the material's ability to recover from an elastic deformation. Examples of elastomers may include, but are not limited to, natural rubbers, polyisoprene, styrene butadiene rubber, chloroprene rubber, polybutadiene, nitrile rubber, butyl rubber, ethylene propylene rubber, ethylene propylene diene monomer, chlorosulfonated polyethylene, polysulfide rubber, polyurethane, EVA film, co-polyester, and silicones. Specific examples of drape 116 materials include a silicone drape, 3M Tegaderm® drape, acrylic drape such as one available from Avery Dennison, or an incise drape. The drape 116 can include an aperture 131 in which interface 133 is inserted. The interface 133 provides fluid communication between the conduit 122 and the sealed space formed by the drape 116.

The term "pad" as used herein generally refers to a substance or structure that is provided to assist in applying reduced pressure to, delivering fluids to, or removing fluids from a tissue site 110. The pad 112 typically includes a plurality of flow channels or pathways that distribute fluids provided to and removed from the tissue site 110 around the pad 112. In one illustrative embodiment, the flow channels or pathways are interconnected to improve distribution of fluids provided or removed from the tissue site 110. The pad 112 may be a biocompatible material that is capable of being placed in contact with the tissue site 110 and distributing reduced pressure to the tissue site 110. Examples of pads 112 may include, for example, without limitation, devices that have structural elements arranged to form flow channels, such as, for example, cellular foam, open-cell foam, porous tissue collections, liquids, gels, and foams that include, or cure to include, flow channels. The pad 112 may be porous and may be made from foam, gauze, felted mat, or any other material suited to a particular biological application. In one embodiment, the pad 112 is a porous foam and includes a plurality of interconnected cells or pores that act as flow channels. The porous foam may be a polyurethane, open-cell, reticulated foam such as GranuFoam® material manufactured by Kinetic Concepts, Incorporated of San Antonio, Tex. Other embodiments might include "closed cells." These closed-cell portions of the pad 112 may contain a plurality of cells, the majority of which are not fluidly connected to adjacent cells. The closed cells may be selectively disposed in the pad 112 to prevent transmission of fluids through perimeter surfaces of the pad 112. In some situations, the pad 112 may also be used to distribute fluids such as medications, antibacterials, growth factors, and various solutions to the tissue site 110. Other layers may be included in or on the pad 112, such as absorptive materials, wicking materials, hydrophobic materials, and hydrophilic materials In some embodiments, the pad 112 includes a compound that reacts with a component of an infecting organism or a product of the infection in the wound 111. As discussed above, the product of the infection can be either from the host (e.g., a compound such as a host protein produced in response to infection, for example a cytokine, a fibronectin fragment, a neutrophil protease, or a macrophage protease) or from the organism (e.g., ATP). In these embodiments, the product of the reaction between the compound and the component of the infecting organism or the product of the infection is drawn into the conduit 122 and detected by the device 118. The device 118 may then notify a data processing system 126, such as a computer, when the product of the reaction is detected via a communications connection 124. The communications connection 124 includes both wire and wireless forms of communication. The data processing system 126 stores the data and may perform calculations to, e.g., calculate the concentration of the measured component or product, or the extent of the infection.

In another embodiment, the device 118 has the reacting compound to detect the component of an infecting organism or a product of the infection; in this embodiment, fluid from the wound 111 is pulled through the pad 112, and into the device 118 to bring the fluid into the presence of the compound. The device 118 may also have the means for measuring the results of the reaction (e.g., charged coupled device [CCD] camera to measure the results from a microarray, chemistry chip or microfluidics device, or photodetector to measure light from the luciferase reaction).

A common product of bacterial infection that may be detected in the illustrative embodiments is adenosine-5'-triphosphate (ATP). In these methods, ATP may be detected by any means known in the art. In some embodiments, ATP is detected using the following luciferase-luciferin reaction, in the presence of $Mg^{+2}$:

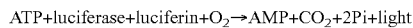

$$ATP + luciferase + luciferin + O_2 \rightarrow AMP + CO_2 + 2Pi + light$$

The light may be visualized, and optionally quantified, using, for example, a photodetector. In one embodiment, the device 118 is a photodetector.

Thus, in some embodiments, the ATP is detected by combining the fluid withdrawn from the wound 111 or an extract thereof with luciferase and luciferin, then measuring the light produced in an ensuing reaction. If the light produced exceeds the light produced by a wound that is not infected, then the wound 111 is infected. In various embodiments, the ATP is quantified by measuring the emitted light, where an increasing amount of ATP in the withdrawn fluid or extract thereof indicates an infection of the wound 111 of increasing severity. See, e.g., U.S. Pat. Nos. 4,833,075; 5,756,303; and 5,916,802 and European patent application 0025351A1 for examples of methods of quantifying ATP to determine the presence of bacteria in a liquid.

In other embodiments, the product of the infection is a host protein associated with an inflammatory response. Any such host protein may be detected by the device 118 in these embodiments. In some of these embodiments, the host protein is a cytokine, a fibronectin fragment, a neutrophil protease, or a macrophage protease. See, e.g., PCT patent publication WO 2004/086043 and U.S. Patent Application Publication US 2005/0079542 A1.

The device 118 can also determine an infection in the wound fluid or extract by assaying for a component of an infecting organism or group of organisms. As used herein, a "component of an infecting organism" is a specifically identifiable piece of an organism capable of causing a wound infection. Nonlimiting examples of such components are lipopolysaccharide (LPS), lipoteichoic acid (LTA), antigens, and DNA having a particular sequence that is characteristic of a specific organism.

In certain embodiments where Gram negative bacteria is to be assayed, the withdrawn fluid or extract thereof is combined with a *limulus* amebocyte lysate, which is sensitive for the lipopolysaccharide (LPS) of Gram negative bacteria. LPS can also be detected, e.g., with antibodies by known immunoassays, including assays that measure endotoxin activity by the priming host neutrophil respiratory burst activity via complement opsonized LPS-IgM immune complexes, such as the Endotoxin Activity Assay™ (Hilmi et al., J. Organ Dysfunction, advanced online publication, 23 Mar. 2009).

In various embodiments where Gram positive bacteria is to be assayed, a component to be assayed is lipoteichoic acid (LTA), which is detected by any means known in the art. In some of these embodiments, the LTA is detected with an assay comprising combining the withdrawn fluid or extract thereof with an antibody that specifically binds to LTA, then determining whether the antibody has bound to LTA.

In some embodiments, the wound fluid or extract thereof is tested for at least one specific genus or species of organism capable of causing a wound infection, e.g., *Streptococcus* sp., or *Streptococcus pyrogenes*. Such tests are desirable when the organism is identified to determine an infection treatment that affects a narrow host range, e.g., when an antibiotic is to be used that has a narrow host target range.

In some embodiments, assaying for a specific genus or species of organism capable of causing a wound infection involves the device 118 identifying, in an extract of the wound fluid, a nucleic acid sequence that is specific for an organism or group of organisms. In some of these methods, the withdrawn fluid is treated to release DNA or RNA from an infecting organism; the DNA, or a cDNA reverse-transcribed from the RNA, is labeled with a detectable label and applied to at least one immobilized nucleic acid specific for the at least one specific organism or group of organisms; and the immobilized nucleic acid is evaluated to determine whether the detectable label is specifically bound thereto. Here, the specific binding of the detectable label to the immobilized nucleic acid indicates that the wound 111 is infected with the specific organism or group of organisms. It is contemplated that microarrays or microfluidics chips can be used for these tests. See, e.g., Affymetrix (2005) Application Notes, Microarray Applications in Infectious Disease, at www.affymetrix.com. In some aspects of these embodiments, the labeled DNA or cDNA is applied to a microarray comprising at least five, ten, twenty, fifty or one hundred immobilized nucleic acids, each nucleic acid specific for a different organism or group of organisms capable of causing a wound infection.

In other embodiments, antibodies or aptamers are used to detect an antigen or aptamer binding site on the organism or group of organisms. In some of these embodiments, the withdrawn fluid or extract thereof is combined with an antibody or aptamer specific for a genus or species of organism of organisms, and the antibody or aptamer is then evaluated to determine whether an antigen from the wound 111 is bound to the antibody or aptamer. Further, multiple antibodies or aptamers can be used to assay for multiple organisms. Thus, in some of these methods, the withdrawn fluid or extract thereof is combined with more than one antibody or aptamer, each antibody or aptamer specific for a different genus or species of organism capable of causing a wound infection; and the more than one antibody or aptamer is then evaluated to determine whether any of the more than one antibody or aptamer is bound to an antigen or aptamer binding site from the wound.

Numerous assays are known in the art for determining whether an antibody or aptamer is bound to an antigen or aptamer binding site. Examples include ELISA, western blot, and the assays described in U.S. Patent Application Publication US 2007/0292397 A1, incorporated herein by reference.

In one embodiment, the device 118 includes a compartment (not shown) for placing a substrate (not shown) comprising bound antibodies such that the fluid flows onto the antibodies as the fluid is drawn from the wound 111. These methods are not limited to any particular substrate for the device 118. Examples include polystyrene microliter plates, nitrocellulose paper, and microchips. In further embodiments, the device comprises a *limulus* amebocyte lysate.

One method for detecting infection in the wound 111 includes subjecting the wound 111 to reduced pressure sufficient to withdraw fluid from the wound 111. The fluid from the wound 111 may be collected in the device 118 or elsewhere, and the withdrawn fluid or an extract thereof may be assayed for a product of the infection or a component of the infecting organism or group of organisms. The presence of the product or component indicates infection in the wound 111. The illustrative embodiments can allow testing of the wound 111 for infection without removal of the dressing 108 for the wound, and detect specific organisms or groups of organisms.

In an alternative embodiment, the system 100 further comprises a reservoir (not shown) adapted for collection of the wound fluids. Such a reservoir may be used to collect fluids that are tested using a separate component of the system 100, such as the device 118. In another example, the device 118 or the reduced-pressure source 128 may have such a reservoir.

Figure 2:
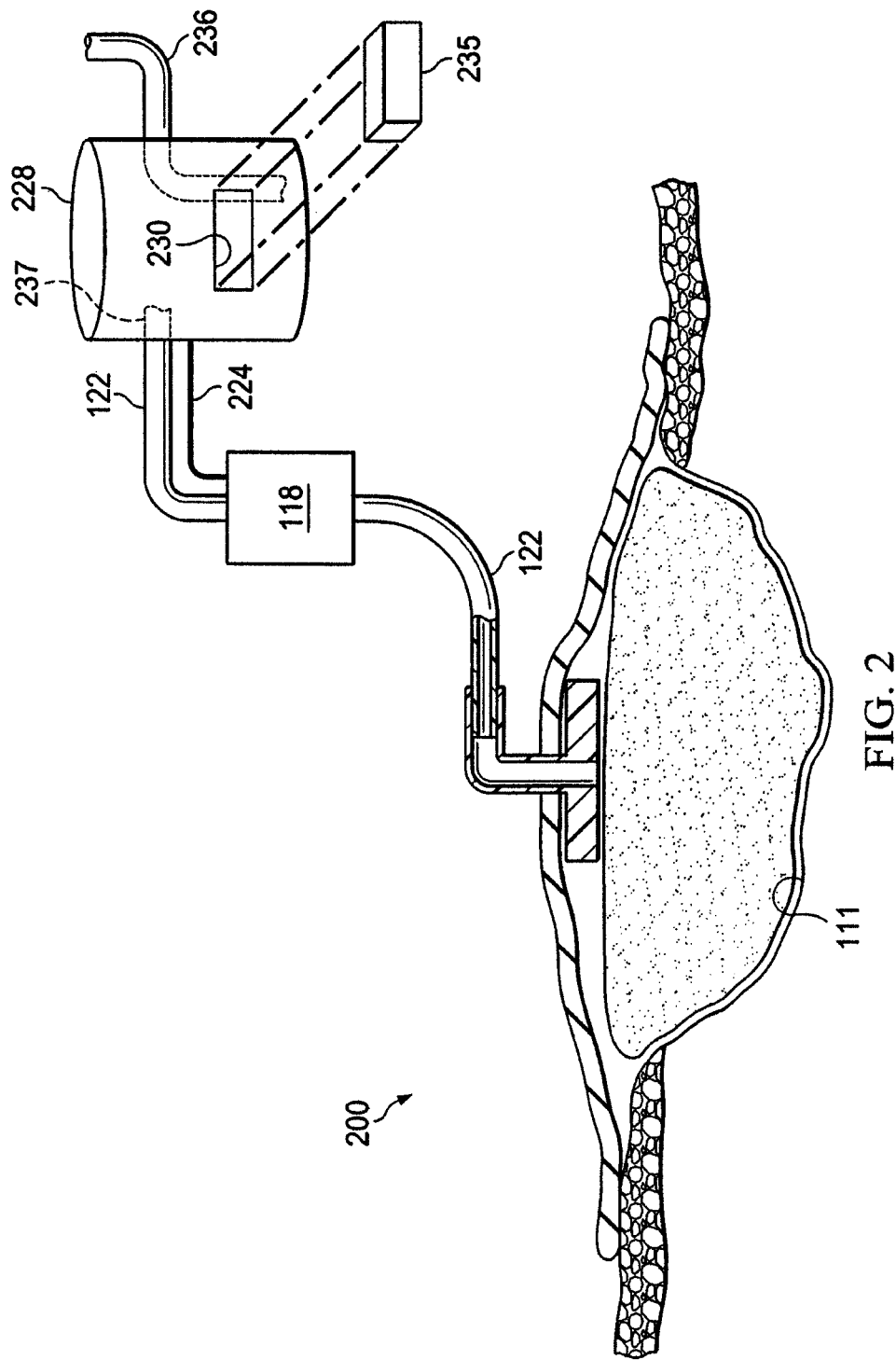
FIG. 2 is a diagram, shown in partial cross-section, of an illustrative embodiment of a reduced-pressure treatment system for detecting infection in which the reduced-pressure source includes a compartment for receiving a chip.

FIG. 2 shows an illustrative embodiment of a reduced-pressure treatment system 200 that includes a reduced-pressure source 228 that comprises a port 230 for a chip 235. The chip 235 may be a microfluidics or microarray or chemistry chip, as well as a detector (e.g., a CCD camera). The chip 235 may be used for detecting specific antigens or nucleic acids characteristic of an organism or group of organisms. The wound fluid is drawn through the conduit 122 to interact with the chip 235 in the port 230. The outlet 237 of the conduit 122 delivers the wound fluid to the chip 235 so that the chip 235 can interact with the wound fluid. The reduced-pressure source 228 can be configured to analyze the microarray or microfluidic data. In some embodiments using microarrays, the labeled DNA or cDNA is applied to a microarray comprising at least five, ten, twenty, fifty or one hundred immobilized nucleic acids, each nucleic acid specific for a different organism or group of organisms capable of causing a wound infection. Excess fluid is then removed through waste conduit 236.

Optionally, the system 200 may also have the device 118 and the communications cable 224. The device 118 or separate data processing system (not shown) can be configured to analyze the microarray or microfluidic data. In the system 200, two measurements can be made on the wound fluid— from the device 118 and from the chip 235 in the port 230.

Figure 3:
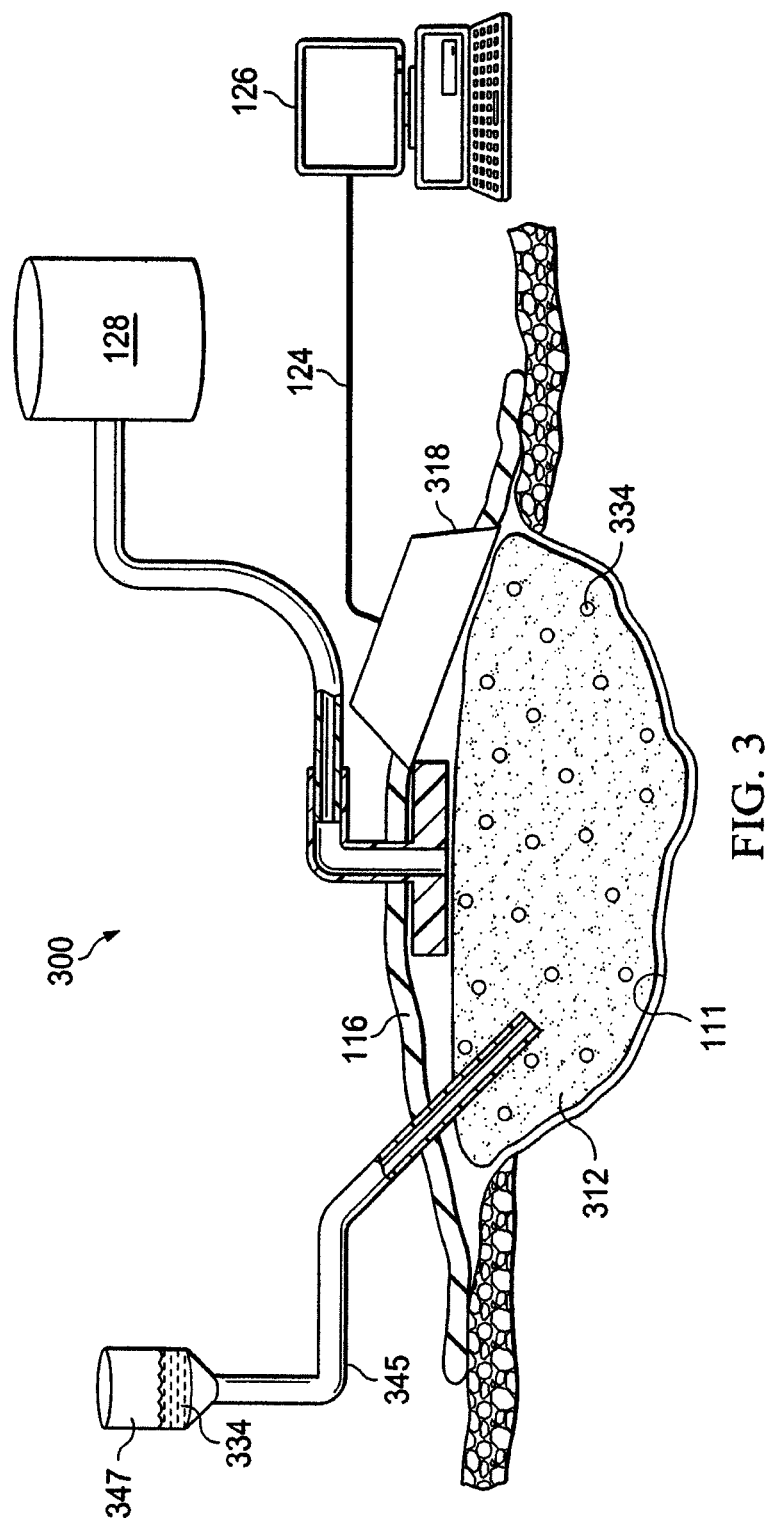
FIG. 3 is a diagram, shown in partial cross-section, of an illustrative embodiment of a reduced-pressure treatment system having a pad that contains a substance.

FIG. 3 is an illustrative embodiment of a reduced-pressure treatment system 300 that includes a pad 312 impregnated with luciferase and luciferin 334. In some embodiments, the luciferase is covalently bound to the pad 312, e.g., as described in U.S. Pat. No. 4,833,075. The reduced-pressure source 128 draws ATP from an infection in the wound 111 into the pad 312, and the ATP reacts with the luciferase and luciferin 334 to generate light. The light generated by the ATP/luciferase/luciferin reaction is detected by the device 318, which comprises a photodetector, and the light measurement is optionally transmitted to the data processing system 126 via the communications connection 124. The data processing system 126 can then record the light measurements. In this manner, the detection of light by the device 318 indicates the presence of ATP in the wound 111.

The device 318 is shown to be integrated with the drape 116. However, the device 318 may be located anywhere in the system 300 at which light from the ATP/luciferase/luciferin reaction can be detected.

In some embodiments, the system 300 further comprises a supply line 345 fluidly connected to the pad 312 for the introduction of luciferase and/or luciferin 334 from a reservoir 347. The supply line 345 may also be used to provide an infection-controlling compound to the wound 111, in which case the reservoir 347 includes such a compound.

It should be apparent from the foregoing that an invention having significant advantages has been provided. While the invention is shown in only a few of its forms, it is not just limited but is susceptible to various changes and modifications without departing from the spirit thereof.

All references cited in this specification are hereby incorporated by reference. The discussion of the references herein is intended merely to summarize the assertions made by the authors and no admission is made that any reference constitutes prior art. Applicants reserve the right to challenge the accuracy and pertinence of the cited references.

We claim:

1. A system for detecting an infection at a wound site, the system comprising:
    a source of reduced pressure;
    a porous pad adapted to deliver the reduced pressure to the wound site;
    a drape adapted to provide a substantially airtight cover over the porous pad and the wound site;
    a conduit fluidly connecting the porous pad to the source of reduced pressure, wherein the conduit is configured to withdraw fluid from the wound site in response to the reduced pressure; and
    a sensor adapted to identify a product of the infection or a component of an infecting organism in fluid withdrawn from the wound site;
    whereby the presence of the product or the component indicates the presence of an infection in the wound.

2. The system of claim 1, wherein the sensor comprises a photodetector and the porous pad further comprises luciferase and luciferin.

3. The system of claim 2, wherein the luciferase is covalently bound to the porous pad.

4. The system of claim 1, wherein the sensor comprises a compartment for placing a substrate comprising bound antibodies, the compartment adapted to allow fluid to flow onto the antibodies as fluid is drawn from the wound.

5. The system of claim 1, wherein the sensor comprises a *limulus* amebocyte lysate.

6. The system of claim 1, wherein the sensor comprises a microarray.

7. The system of claim 6, wherein the microarray is in the reduced pressure source.

8. The system of claim 1, further comprising a computer capable of recording data from the sensor.

9. A porous pad adapted for distributing reduced pressure to a wound site, wherein the pad comprises luciferase.

10. The porous pad of claim 9, wherein the luciferase is covalently bound to the pad.

11. The porous pad of claim 9, further comprising luciferin.

* * * * *